(12) United States Patent
Uchida

(10) Patent No.: US 7,714,142 B2
(45) Date of Patent: May 11, 2010

(54) PROCESS FOR PRODUCTION OF (4,5-DIHYDROISOXAZOL-3-Y) THIO-CARBOXAMIDINE SALTS

(75) Inventor: Yukio Uchida, Ihara-gun (JP)

(73) Assignee: Ihara Chemical Industry Co., Ltd., Tokyo (JP)

( * ) Notice: Subject to any disclaimer, the term of this patent is extended or adjusted under 35 U.S.C. 154(b) by 484 days.

(21) Appl. No.: 11/722,256

(22) PCT Filed: Dec. 19, 2005

(86) PCT No.: PCT/JP2005/023270

§ 371 (c)(1),
(2), (4) Date: Jun. 20, 2007

(87) PCT Pub. No.: WO2006/068092

PCT Pub. Date: Jun. 29, 2006

(65) Prior Publication Data

US 2008/0275249 A1  Nov. 6, 2008

(30) Foreign Application Priority Data

Dec. 20, 2004  (JP) .............................. 2004-367418

(51) Int. Cl.
*C07D 261/04* (2006.01)
(52) U.S. Cl. ...................... 548/243; 548/240
(58) Field of Classification Search ................ 548/240, 548/243
See application file for complete search history.

(56) References Cited

U.S. PATENT DOCUMENTS 7,256,298 B2 * 8/2007 Nakatani et al. ......... 548/366.1
7,488,831 B2 * 2/2009 Uchida .................... 548/366.1

FOREIGN PATENT DOCUMENTS

| JP | 2004 224714 | 8/2004 |
|----|-------------|--------|
| WO | 02 062770   | 8/2002 |
| WO | 03 000686   | 1/2003 |
| WO | 2005 095352 | 10/2005 |
| WO | 2005 105755 | 11/2005 |

OTHER PUBLICATIONS

Dovlatyan, et al., "The synthesis of 2-oxo-4-chloro-1,2,3-oxathiazole-$\Delta^3$ and its 5,5-dimethyl derivative and their conversions", Armyanskii Khimicheskii Zhurnal, vol. 28, No. 3. pp. 233-238, 1975. (with English abstract).

Dovlatyan, et al., "The synthesis of 2,2 dioxo-4-chloro-1,2,3-oxathiazole-$\Delta^2$ and its 5,5-dimethyl-derivative and their conversions", Armyanskii Khimicheskii Zhurnal, vol. 28, No. 4, pp. 311-316, 1975. (with English abstract).

Dovlatyan, et al., "The synthesis of 1-oxo(1, 1-dioxo)-3-chloro-4,4-dimethyl-1,2,5-Thiadiazole-$\Delta^2$ and its Transformations", Armyanskii Khimicheskii Zhurnal, vol. 28, No. 5, pp. 412-416, 1975. (with English abstract).

* cited by examiner

*Primary Examiner*—Golam M Shameem
(74) *Attorney, Agent, or Firm*—Oblon, Spivak, McClelland, Maier & Neustadt, L.L.P.

(57) ABSTRACT

To provide a method for producing a (4,5-dihydroisoxazol-3-yl)thiocarboxamidine salt compound simply, safely and in good yield, whereby drawbacks of prior art have been solved.

A method for producing a (4,5-dihydroisoxazol-3-yl)thiocarboxamidine salt compound of the formula (2):

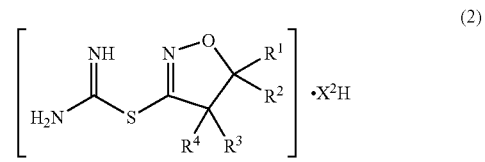

(2)

wherein each of $R^1$ and $R^2$ which are independent of each other, is a hydrogen atom, an alkyl group or a cycloalkyl group, each of $R^3$ and $R^4$ which are independent of each other, is a hydrogen atom or an alkyl group, provided that $R^1$ and $R^2$, or $R^2$ and $R^3$, may be bonded to each other to form a cycloalkyl group together with the carbon atoms to which they are bonded, and $X^2$ is a halogen or an anionic residue derived from an acid, which comprises reacting a 3-halogeno-4,5-dihydroisoxazole compound of the formula (1):

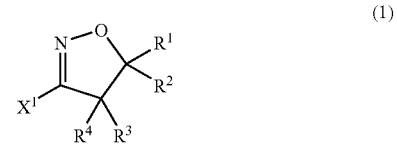

(1)

wherein $R^1$, $R^2$, $R^3$ and $R^4$ are as defined above, and $X^1$ is a halogen, with thiourea in the presence of an acid.

13 Claims, No Drawings

PROCESS FOR PRODUCTION OF (4,5-DIHYDROISOXAZOL-3-Y) THIO-CARBOXAMIDINE SALTS

TECHNICAL FIELD

The present invention relates to a method for producing a (4,5-dihydroisoxazol-3-yl)thiocarboxamidine salt compound which is useful as an intermediate for the production of pharmaceuticals and agricultural chemicals.

BACKGROUND ART

The (4,5-dihydroisoxazol-3-yl)thiocarboxamidine salt compound obtained by the present invention, can easily be led to a 4,5-dihydroisoxazolidine-3-thiol analogue which is useful as an intermediate for the production of pharmaceuticals and agricultural chemicals, by carrying out hydrolysis under a basic condition.

Heretofore, a literature is known which discloses that an isoxazoline-3-thione derivative can be obtained by reacting a 3-halogeno-4,5-dihydroisoxazole compound with thiourea (Patent Document 1).

However in the Patent Document 1 there is no disclosure with respect to use of an acid in the reaction of the 3-halogeno-4,5-dihydroisoxazole compound with thiourea, or with respect to the production of a (4,5-dihydroisoxazol-3-yl)thiocarboxamidine salt compound.

Patent Document 1: JP-A-2004-224714

DISCLOSURE OF THE INVENTION

Problem to be Solved by the Invention

The present invention is to provide a method for producing a (4,5-dihydroisoxazol-3-yl)thiocarboxamidine salt compound simply, safely and in good yield.

Means to Solve the Problem

Under the circumstances, the present inventors have conducted an extensive study on a method for producing a (4,5-dihydroisoxazol-3-yl)thiocarboxamidine salt compound and as a result, have found it possible to form a (4,5-dihydroisoxazol-3-yl)thiocarboxamidine salt compound in a short time and in good yield by reacting a 3-halogeno-4,5-dihydroisoxazole compound with thiourea in the presence of an acid. The present invention has been accomplished on the basis of this discovery.

Thus, the present invention provides the following:

(1) A method for producing a (4,5-dihydroisoxazol-3-yl)thiocarboxamidine salt compound of the formula (2):

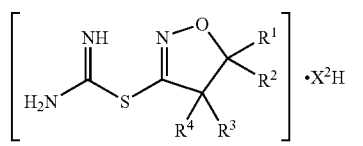

wherein each of $R^1$ and $R^2$ which are independent of each other, is a hydrogen atom, an alkyl group or a cycloalkyl group, each of $R^3$ and $R^4$ which are independent of each other, is a hydrogen atom or an alkyl group, provided that $R^1$ and $R^2$, or $R^2$ and $R^3$, may be bonded to each other to form a cycloalkyl group together with the carbon atoms to which they are bonded, and $X^2$ is a halogen or an anionic residue derived from an aced, which comprises reacting a 3-halogeno-4,5-dihydroisoxazole compound of the formula (1):

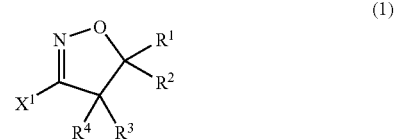

wherein $R^1$, $R^2$, $R^3$ and $R^4$ are as defined above, and $X^1$ is a halogen, with thiourea in the presence of an acid.

(2) The method for producing a (4,5-dihydroisoxazol-3-yl)thiocarboxamidine salt compound according to (1) wherein the acid is an inorganic acid.

(3) The method for producing a (4,5-dihydroisoxazol-3-yl)thiocarboxamidine salt compound according to (1), wherein the acid is hydrochloric acid, hydrobromic acid or a mixture thereof.

(4) The method for producing a (4,5-dihydroisoxazol-3-yl thiocarboxamidine salt compound according to any one of (1) to (3), wherein in the formula (1), each of $R^1$ and $R^2$ is an alkyl group, each of $R^3$ and $R^4$ is a hydrogen atom, and $X^1$ is a chlorine atom.

(5) The method for producing a (4,5-dihydroisoxazol-3-yl)thiocarboxamidine salt compound according to any one of (1) to (3), wherein in the formula (X), each of $R^1$ and $R^2$ is a methyl group, each of $R^3$ and $R^4$ is a hydrogen atom, and $X^1$ is a chlorine atom.

(6) The method for producing a (4,5-dihydroisoxazol-3-yl)thiocarboxamidine salt compound according to any one of (1) to (3) wherein in the formula (X) each of $R^1$ and $R^2$ is an alkyl group, each of $R^3$ and $R^4$ is a hydrogen atom, and $X^1$ is a bromine atom.

(7) The method for producing a (4,5-dihydroisoxazol-3-yl)thiocarboxamidine salt compound according to any one of (1) to (3), wherein in the formula (a), each of $R^1$ and $R^2$ is a methyl group, each of $R^3$ and $R^4$ is a hydrogen atom, and $X^1$ is a bromine atom.

(8) A (4,5-dihydroisoxazol-3-yl)thiocarboxamidine salt compound of the formula (2):

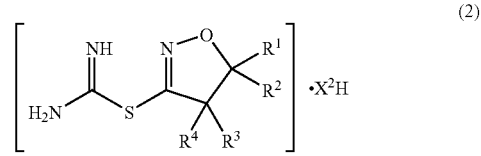

wherein each of $R^1$ and $R^2$ which are independent of each other, is a hydrogen atom, an alkyl group or a cycloalkyl group, each of $R^3$ and $R^4$ which are independent of each other, is a hydrogen atom or an alkyl group, provided that $R^1$ and $R^2$, or $R^2$ and $R^3$ may be bonded to each other to form a cycloalkyl group together with the carbon atoms to which they are bonded, and $X^2$ is a halogen or an anionic residue derived from an acid.

(9) A 4,5-dihydroisoxazol-3-yl)thiocarboxamidine salt compound of the formula (3):

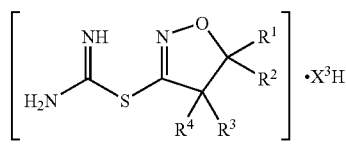

wherein each of $R^1$ and $R^2$ which are independent of each other, is a hydrogen atom, an alkyl group or a cycloalkyl group, each of $R^3$ and $R^4$ which are independent of each other, is a hydrogen atom or an alkyl group, provided that $R^1$ and $R^2$, or $R^2$ and $R^3$, may be bonded to each other to form a cycloalkyl group together with the carbon atoms to which they are bonded, and $X^3$ is a halogen.

(10) The (4,5-dihydroisoxazol-3-yl)thiocarboxamidine salt compound according to (8) or (9), wherein each of $R^1$ and $R^2$ is a methyl group, and each of $R^3$ and $R^4$ is a hydrogen atom.

(11) [5,5-dimethyl-(4,5-dihydroisoxazol-3-yl)]thiocarboxamidine hydrochloride.

(12) [5,5-dimethyl-(4,5-dihydroisoxazol-3-yl)]thiocarboxamidine hydrobromide.

Effects of the Invention

By the method of the present invention, a (4,5-dihydroisoxazol-3-yl)thiocarboxamidine salt compound of the formula (2) given hereinafter, can be produced in a short time and in good yield. Further, the obtained (4,5-dihydroisoxazol-3-yl) thiocarboxamidine salt can be easily converted to an alkali metal salt of a 4,5-dihydroisoxazolidine-3-thiol compound which is useful as an intermediate for pharmaceuticals and agricultural chemicals by alkali hydrolysis. Thus, the (4,5-dihydroisoxazol-3-yl)thiocarboxamidine salt compound of the formula (2) is a good raw material for the production of an alkali metal salt of a 4,5-dihydroisoxazolidine-3-thiol compound as an intermediate for pharmaceuticals and agricultural chemicals. In the method of the present invention, handling of the raw material is simple, and thus the method is very useful as an industrial production method.

BEST MODE FOR CARRYING OUT THE INVENTION

Now, the method for producing a (4,5-dihydroisoxazol-1-yl)thiocarboxamidine salt compound according to the above (1) to (7) will be described.

The method of the present invention is a method for producing a (4,5-dihydroisoxazol-3-yl)thiocarboxamidine salt compound of the formula (2) in a short time and in good yield by reacting a 3-halogeno-4,5-dihydroisoxazole compound of the formula (1) with thiourea, which is characterized in that an acid is used for the reaction. The (4,5-dihydroisoxazol-3-yl)thiocarboxamidine salt compound obtained by this reaction is a novel compound and is a good raw material for the production of an alkali metal salt of a 4,5-dihydroisoxazolidine-3-thiol compound which is an intermediate for pharmaceuticals and agricultural chemicals.

Firstly, the raw material compound of the formula (1) to be used as a raw material in the method of the present invention, will be described.

A notation such as "$C_{1-6}$" to be used in this specification indicates that, in this case, the number of carbon atoms in the substituent following this notation is from 1 to 6.

In the formula (1), each of $R^1$ and $R^2$ which are independent of each other, is a hydrogen atom, an alkyl group or a cycloalkyl group, each of $R^3$ and $R^4$ which are independent of each other, is a hydrogen atom or an alkyl group, provided that $R^1$ and $R^2$, or $R^2$ and $R^3$, may be bonded to each other to form a cycloalkyl group, together with the carbon atoms to which they are bonded.

Here, the alkyl group is preferably a linear or branched alkyl group having from 1 to 6 carbon atoms, and may, for example, be a methyl group, an ethyl group, a n-propyl group, an isopropyl group, a n-butyl group, an isobutyl group, a sec-butyl group, a tert-butyl group, a n-pentyl group, an isopentyl group, a neopentyl group, a n-hexyl group, an isohexyl group or a 3,3-dimethylbutyl group.

The cycloalkyl group is preferably an alkyl group having from 3 to 6 carbon atoms (a $C_{3-6}$ cycloalkyl group) and may, for example, be a cyclopropyl group, a cyclopentyl group or a cyclohexyl group.

With respect to preferred substituents in the formula (1) of the present invention, each of $R^1$ and $R^2$ which are independent of each other, is a $C_{1-6}$ alkyl group, and more preferred $R^1$ or $R^2$ is a methyl group or an ethyl group, and each of $R^3$ and $R^4$ is preferably a hydrogen atom.

In the formula (1), $X^1$ is a halogen.

Here, the halogen represents a halogen such as bromine, chlorine, fluorine or Iodine.

The 3-halogeno-4,5-dihydroisoxazole compound of the formula (1) to be used in the method of the present invention may be any compound so long as it is a compound represented by the formula (1). Specifically, 3-chloro-5,5-dimethyl-4,5-dihydroisoxazole or 3-bromo-5,5-dimethyl-4,5-dihydroisoxazole may, for example, be mentioned as a representative example.

The 3-halogeno-4,5-dihydroisoxazole compound of the formula (1) is a known compound or a compound which can be produced by subjecting a halogeno oxime compound and a corresponding olefin compound to a 1,3-dipolar cycloaddition reaction in accordance with a known method.

The reaction in the method of the present invention is carried out by using thiourea. The amount of thiourea to be used, may be at any level so long as the reaction proceeds sufficiently. However, it is, for example, within a range of from 1.0 to 100 mols, preferably from 1.0 to 10 mols, more preferably from 1.0 to 2 mols, per mol of the 3-halogeno-4,5-dihydroisoxazole compound of the formula (1). In this reaction, 1 mol of thiourea to 1 mol of the 3-halogeno-4,5-dihydroisoxazole compound of the formula (1) will be 1 equivalent.

The reaction in the method of the present invention is carried out in the presence of an acid. The acid useful may, for example, be an organic acid represented by an organic sulfonic acid such as p-toluene sulfonic acid, methane sulfonic acid or benzene sulfonic acid; or an inorganic acid including a hydrohalogenic acid represented by hydrochloric acid or hydrobromic acid, or sulfuric acid or phosphoric acid. These acids may be used alone or in combination as a mixture. Preferred is a hydrohalogenic acid such as hydrochloric acid or hydrobromic acid, and particularly preferred is hydrochloric acid which is inexpensive and simple in handling. When hydrochloric acid is to be used, the concentration is usually from 1 to 37%, preferably from 35 to 37%, although it depends also on the temperature. The anionic residue derived from such an acid may, for example, be an organic anion such as a p-toluene sulfonyloxyanion, a methane sulfonyloxyanion or a benzene sulfonyloxyanion, a halogen anion such as a chloroanion, a bromoanion or an iodoanion, or an inorganic anion such as sulfuric anion, a hydrogen sulfate anion, a phosphoric anion, a dihydrogen phosphate anion or a monohydrogen phosphate anion.

The amount of the acid to be used for the reaction in the method of the present invention may be any amount so long as it is an amount whereby the reaction proceeds sufficiently. However, it is usually from 0.05 to 100 mols, preferably from 0.1 to 10 mols, more preferably from 0.5 to 1.5 mols, per mol of the 3-halogeno-4,5-dihydroisoxazole compound of the formula (1).

The solvent which may be used for the reaction in the method of the present invention may be any solvent so long as it does not hinder the reaction. It may, for example, be water; an alcohol such as methanol ethanol or isopropyl alcohol; an aromatic hydrocarbon such as toluene, xylene or chlorobenzene; a halogenated aliphatic hydrocarbon such as dichloromethane or chloroform; an aliphatic acid ester represented by an acetic acid ester such as methyl acetate, ethyl acetate or butyl acetate; a ketone such as acetone, methyl ethyl ketone (MEK) or methyl isobutyl ketone (MIBK); an aprotic polar solvent such as acetonitrile, dimethylformamide (DMF), dimethylacetamide (DMAC), N-methylpyrrolidone, tetramethylurea, hexamethylphosphoric triamide (HMPA) or propylene carbonate; an ether type solvent such as ethyl ether, isopropyl ether, tetrahydrofuran or dioxane; or an aliphatic hydrocarbon such as pentane or n-hexane.

These solvents may be used alone or in combination as a mixed solvent with an optional mixing ratio. For example, if the present reaction is carried out in a mixed solvent system having a solvent having a high polarity such as an alcohol such as isopropyl alcohol, mixed with a solvent having a low polarity, the reaction will be accelerated and in many cases, good results can be obtained such that the reaction time can be shortened, and the yield will be improved.

The amount of such a solvent may be at such a level that stirring of the reaction system can be sufficiently carried out. However, the solvent is usually in an amount within a range of from 0.05 to 10 liters, preferably from 0.5 to 2 liters, per mol of the 3-halogeno-4,5-dihydroisoxazole compound of the formula (1).

The temperature for the reaction in the method of the present invention may, for example, be within a range of from 0° C. to the reflux temperature of the solvent to be used, preferably within a range of from 20° C. to 50° C.

The time for the reaction in the method of the present invention is not particularly limited but it is preferably from one hour to 10 hours from the viewpoint of suppression of by-products, etc.

By the method of the present invention, the (4,5-dihydroisoxazol-3-yl)thiocarboxamidine salt compound of the formula (2) will be formed highly selectively under a mild condition without requiring a special reaction apparatus. The (4,5-dihydroisoxazol-3-yl)thiocarboxamidine salt compound obtained by the method of the present invention, can easily be led to a 4,5-dihydroisoxazolidine-3-thiol analogue useful as an intermediate for the production of pharmaceuticals and agricultural chemicals, by carrying out hydrolysis under a basic condition.

Now, the compound of the present invention (the (4,5-dihydroisoxazol-3-yl)thiocarboxamidine salt compound) as defined in (8) to (12), will be described.

The compound of the present invention can be produced by the method as described in the above (1) to (7).

Here, in a case where the acid used for the production of the compound of the present invention is a polybasic acid such as sulfuric acid or phosphoric acid, the compound of the present invention has a number of the (4,5-dihydroisoxazol-3-yl)thiocarboxamidine structure (the structure drawn in the brackets [ ] in the formula (2)) corresponding to the valence of such a polybasic acid. Even in such a case, the structure of the (4,5-dihydroisoxazol-3-yl)thiocarboxamidine salt compound is represented by the formula (2) irrespective of the valence of such an acid ($X^2H$).

Further, in a case where in the production of the compound of the present invention, as the acid, a hydrohalogenic acid having the same halogen as $X^1$ of the 3-halogeno-4,5-dihydroisoxazole compound of the formula (1) to be used as a raw material is used alone, the acid represented by $X^2H$ in the formula (2) represents a single acid. However, in a case where an acid having a halogen or an anionic residue different from $X^1$ in the formula (1), is used, or in a case where two or more acids are used, the acid (the acid represented by $X^2H$ in the formula (2)) which the compound of the present invention has, may be a mixture having two or more acids mixed, and the compound of the present invention is one which includes a salt having such two or more acids mixed.

Specific examples of the compound of the present invention will be exemplified in the following Table 1, but it should be understood that the compound of the present invention is not limited to such exemplified compounds and includes all of the compounds represented by the formula (2).

The abbreviations in Table 1 have the following meanings, respectively.

Me: methyl group

Et: ethyl group

Pr: n-propyl group iPr: isopropyl group

Bu: n-butyl group cHex: cyclohexyl group

TABLE 1

| Compound number | $R^1$ | $R^2$ | $R^3$ | $R^4$ | $X^2H$ |
|---|---|---|---|---|---|
| 1 | Me | Me | H | H | HCl |
| 2 | Me | Me | H | H | HBr |
| 3 | Me | Me | H | H | HCl + HBr |
| 4 | Me | Me | H | H | $H_2SO_4$ + HBr |
| 5 | Me | Me | H | H | Phosphoric acid + HBr |
| 6 | Me | Me | H | H | Methane sulfonic acid + HBr |
| 7 | Me | Me | H | H | p-Toluene sulfonic acid + HBr |
| 8 | Me | H | Me | H | HCl |
| 9 | Bu | H | H | H | HBr |
| 10 | Pr | H | Et | H | HBr |
| 11 | iPr | H | Me | H | HBr |
| 12 | Me | H | iPr | H | HBr |
| 13 | Me | Me | Me | Me | HBr |
| 14 | Me | Pr | H | H | HBr |
| 15 | cHex | H | H | H | HBr |
| 16 | H | —$(CH_2)_3$— | | H | HBr |
| 17 | Me | —$(CH_2)_4$— | | H | HCl |
| 18 | —$(CH_2)_4$— | | H | H | HBr |
| 19 | H | H | H | H | HCl |

Now, the method for producing the compound of the present invention will be described in detail with reference to Examples. However, it should be understood that the present invention is by no means restricted to such Examples.

Reference Example 1

Preparation of
3-chloro-5,5-dimethyl-4,5-dihydroisoxazole

In 500 ml of ethanol, 63.0 g (0.75 mol) of sodium hydrogen carbonate was added, followed by stirring at room temperature. While 84.2 g (1.50 mol) of isobutene gas was blown thereinto, upon expiration of 0.5 hour, the temperature was raised to 70° C., and then, 131.3 g (0.5 mol) of a 40% isopropyl ether solution of dichloroform oxime, was gradually dropwise added to the reaction solution, followed by stirring at the same temperature for 8 hours. The reaction solution was left to cool to at most 25° C., and an inorganic solid was removed by filtration, followed by distillation under reduced pressure at 62° C./1.1 kPa, to obtain 32.3 g (yield: 51%) of 3-chloro-5,5-dimethyl-4,5-dihydroisoxazole as a colorless transparent liquid.

$^1$H-NMR (300 MHz, MeOH-d4): δ=2.88 (s, 2H), 1.41 (s, 3H) ppm

GC-MS (EI): m/z=133 (M$^+$), 118 (base)

Boiling point: 50° C./0.7 kPa

DSC measurement (calorific value: 1,718 mJ/mg, initiation temperature of heat generation: 170° C.)

Reference Example 2

Preparation of
3-bromo-5,5-dimethyl-4,5-dihydroisoxazole 84.0 g (2.1 mol) of 99% sodium hydroxide in the form of beads, was suspended in 350 ml of isopropyl ether and cooled to a temperature of at most 5° C. With stirring under cooling with ice, blowing of 2-methylpropene was started at a rate such that blowing of 78.6 g (1.4 mol) would be completed in about three hours. One hour later, after confirming that 26.2 g (0.47 mol; ⅓ of the designed amount) of 2-methylpropene was blown, while 2-methylpropene was introduced continuously at the same rate, 464.0 g (concentration: 30.6%) of an isopropyl ether solution of dibromoform oxime was dropwise added over a period of 3 hours with stirring under cooling to a temperature of at most 5° C. After completion of the dropwise addition, aging was carried out at the same temperature for two hours. To the reaction solution, 350 ml of water was added, followed by stirring at room temperature for 0.5 hour, whereupon the organic layer was separated. The obtained organic layer was washed twice with 140 ml of water and once with 70 ml of a saturated sodium chloride solution and dried over anhydrous sodium sulfate. The solvent was distilled off, and the obtained yellow oil was further distilled to obtain 84.7 g (purity: 99.0%, yield: 68%) of 3-bromo-5,5-dimethyl-4,5-dihydroisoxazole as a transparent liquid.

$^1$H-NMR (300 MHz, CDCl$_3$): δ=2.95 (s, 2H), 1.44 (s, 3H) ppm

GC-MS (EI): m/z=178 (M$^+$) 162 (base)

Boiling point: 4° C./0.3 kPa

DSC measurement (calorific value: 1,879 mJ/mg, initiation temperature of heat generation: 165° C.)

Example 1

Preparation of [5,5-dimethyl(4,5-dihydroisoxazol-3-yl)]thiocarboxamidine hydrochloride To a solution of 16.8 g (0.2 mol) of thiourea in 100 ml (0.5 l/mol) of ethanol, 4.17 g (0.04 mol) of 35% hydrochloric acid was added, and with stirring at room temperature, 26.7 g (0.2 mol) of 3-chloro-5,5-dimethyl-4,5-dihydroisoxazol was dropwise added over a period of one hour, followed by stirring at 30° C. for 3 hours. Then, to the reaction solution, 100 ml of toluene was added, and the solvent was distilled off under reduced pressure, whereby 58.3 g of white crystals were precipitated. To the obtained crude crystals, 300 ml of isopropyl alcohol was added, followed by heating until the crystals were dissolved, and then the solution was gradually cooled to obtain 38.5 g (yield: 92.0%) of the above-identified compound as white crystals.

IR (KBr, cm$^{-1}$) 3,000-3,300 (amine), 1,664 (N=C),

DSC measurement (calorific value: 1,204 mJ/ma, initiation temperature of heat generation: 143° C.)

Using the [5,5-dimethyl(4,5-dihydroisoxazol-3-yl)]thiocarboxamidine hydrochloride obtained here, as a standard sample, the reaction yield was, hereinafter, calculated by an external standard method of high performance liquid chromatography.

Example 2

Preparation of [5,5-dimethyl(4,5-dihydroisoxazol-3-yl)]thiocarboxamidine hydrobromide To a solution of 22.8 g 10.3 mol) of thiourea in 100 ml (0.5 l/mol) of acetonitrile, 48.6 g (0.3 mol) of 50% hydrobromic acid was added, and with stirring at room temperature, 35.6 g (0.2 mol) of 3-bromo-5,5-dimethyl-4,5-dihydroisoxazole was dropwise added over a period of one hour, followed by stirring at 30° C. for 5 hours. Precipitated crystals were subjected to suction filtration to obtain 81.1 g (yield: 95.0%, purity: 90%) of the above-identified compound as white crystals. The obtained crystals were re-crystallized from n-hexane/isopropyl alcohol (10/1) to obtain 61.4 g (yield: 80.0%, purity: 99%) of the above-identified compound with high purity.

IR (KBr, cm$^{-1}$) 3,000-3,300 (amine), 1,664 (N=C),

DSC measurement (calorific value: 821 mJ/mg, initiation temperature of heat generation: 152° C.)

Using the [5,5-dimethyl(4,5-dihydroisoxazol-3-yl)]thiocarboxamidine hydrobromide obtained here, as a standard sample, the reaction yield was, hereinafter, calculated by an external standard method of high performance liquid chromatography.

Example 3

Preparation of [5,5-dimethyl(4,5-dihydroisoxazol-3-yl)]thiocarboxamidine hydrochloride aqueous solution To a solution of 22.8 g (0.3 mol) of thiourea in 100 ml (0.5 l/mol) of acetonitrile, 48.6 g (0.3 mol) of 50% hydrobromic acid was added, and with stirring at room temperature, 200.0 g (0.2 mol, concentration: 17.8%) of an isopropyl ether solution of 3-bromo-5,5-dimethyl-4,5-dihydroisoxazole was dropwise added over a period of one hour, followed by stirring at 30° C. for 5 hours. To the reaction solution, 100 ml (0.5 l/mol) of water was added, and 305 g of an aqueous layer was separated. The obtained aqueous layer was analyzed by the external standard method of high performance liquid chromatography based on the standard sample obtained in Example 2, whereby in this aqueous layer, the above-identified compound was contained at a concentration of 15.0%, and the yield was 90%.

Examples 4 to 17

Using the 3-halogeno-5,5-dimethyl-4,5-dihydroisoxazole compound represented by the following formula as the raw material, the reactions were carried out in the same manner as in Example 3 in various combinations of the solvent and the acid, and the yields were calculated by the external standard method of high performance liquid chromatography. The results are shown in Table 2.

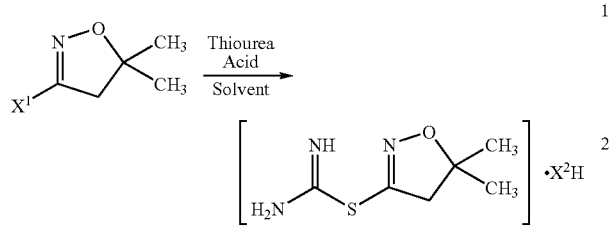

In the above formulae, $X^1$ and $X^2$ are as defined above lyzed by high performance liquid chromatography, whereby the above-identified compound was found to be obtained in an amount of only 10% by the total area value.

Reference Example 3

Preparation of sodium salt of [5,5-dimethyl(4,5-dihydroisoxazol-3-yl)]thiol

In 15 ml of ethanol, 3.3 g (0.0156 mol) of [5,5-dimethyl(4,5-dihydroisoxazol-3-yl)]thiocarboxamidine hydrochloride and 0.6 g (0.0153 mol) of 99% sodium hydroxide were added under cooling with water bath, followed by stirring for 3 hours. After distilling off ethanol under reduced pressure, the obtained viscous substance was washed twice with 10 ml of diethyl ether and twice with 10 ml of acetonitrile to obtain 2.3 g of white powdery crystals.

IR (KBr, cm$^{-1}$) 1,664 (N=C)

Reference Example 4

Preparation of 3-methylthio-4,5-dihydro-5,5-dimethylisoxazole 1 ml of methyl iodide was added to 2.0 g of the sodium salt of [5,5-dimethyl(4,5-dihydroisoxazol-3-yl)]thiol obtained in

TABLE 2

| | X | Solvent (amount: l/mol) | Acid (amount) | Thiourea (equivalent) | Time (hr) | Yield (%) |
|---|---|---|---|---|---|---|
| Ex. 4 | Cl | Ethanol (1) | 35% HCl (0.2 equivalent) | 1.1 | 9 | 90 |
| Ex. 5 | Cl | Ethanol (1) | 35% HCl (1.2 equivalent) | 1.1 | 5 | 92 |
| Ex. 6 | Cl | Isopropanol (1) | 35% HCl (1.2 equivalent) | 1.5 | 1 | 94 |
| Ex. 7 | Br | Water (1) | 48% HBr (1.2 equivalent) | 1.1 | 5 | 63 |
| Ex. 8 | Br | IPE*[1](1) + Methanol (0.5) | 48% HBr (1.2 equivalent) | 1.1 | 1 | 81 |
| Ex. 9 | Br | IPE(1) + Ethanol (0.5) | 48% HBr (1.2 equivalent) | 1.1 | 1 | 86 |
| Ex. 10 | Br | IPE(1) + IPA*[2](0.5) | 48% HBr (0.2 equivalent) | 1.1 | 10 | 85 |
| Ex. 11 | Br | IPE(1) + IPA(0.5) | 48% HBr (1.2 equivalent) | 1.1 | 5 | 85 |
| Ex. 12 | Br | IPE(1) + IPA(0.5) | 48% HBr (1.2 equivalent) | 2.2 | 1 | 91 |
| Ex. 13 | Br | IPE(1) + Acetone (0.5) | 48% HBr (1.2 equivalent) | 1.1 | 1 | 89 |
| Ex. 14 | Br | IPE(1) + Acetonitrile (0.5) | 35% HCl (1.2 equivalent) | 1.5 | 3 | 96 |
| Ex. 15 | Br | IPE(1) + Acetonitrile (0.5) | 99% $H_2SO_4$ (1.2 equivalent) | 1.5 | 3 | 90 |
| Ex. 16 | Br | IPE(1) + Acetonitrile (0.5) | Methane sulfonic acid (1.2 equivalent) | 1.5 | 3 | 88 |
| Ex. 17 | Br | MIBK*[3](1) | 35% HCl (1.0 equivalent) | 1.1 | 5 | 92 |

*[1]"IPE" represents isopropyl ether.
*[2]"IPA" represents isopropyl alcohol.
*[3]"MIBK" represents methyl isobutyl ketone.

Comparative Example

Preparation of [5,5-dimethyl(4,5-dihydroisoxazol-3-yl)]thiocarboxamidine hydrochloride To a solution of 16.8 g (0.2 mol) of thiourea in 100 ml (0.5 l/mol) of ethanol, 26.7 g (0.2 mol) of 3-chloro-5,5-dimethyl-4,5-dihydroisoxazole was dropwise added over a period of one hour with stirring at room temperature, followed by stirring at 30° C. for 10 hours. The reaction solution was ana- Reference Example 3, followed by stirring for 0.5 hour. The obtained solution was distilled under reduced pressure to obtain 2 g of the above-identified compound.

$^1$H-NMR (400 MHz, CDCl$_3$): δ=2.79 (s, 2H), 2.49 (s, 3H), 1.42 (s, 3H) ppm

GC-MS (EI): m/z=145 (M$^+$)

Boiling point: 103 to 110° C./2.7 kPa

DSC measurement (calorific value-849 mJ/mg, initiation temperature of heat generation 241° C.)

INDUSTRIAL APPLICABILITY

The present invention provides a novel industrial method for producing a (4,5-dihydroisoxazol-3-yl)thiocarboxamidine salt compound. According to the method of the present invention, it is possible to produce a (4,5-dihydroisoxazol-3-yl)thiocarboxamidine salt compound of the formula (2) by a simple operation method under a mild condition and in good yield from a 3-halogeno-4,5-dihydroisoxazole compound of the formula (1). By the effects of an acid, the reaction can be completed in a short time in good yield, and thus the method is very useful as an industrial production method.

The invention claimed is:

1. A method for producing a (4,5-dihydroisoxazol-3-yl)thiocarboxamidine salt compound of formula (2):

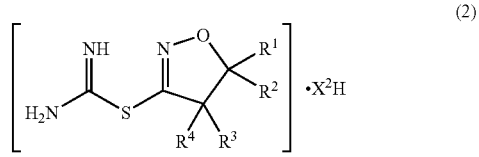

(2)

wherein each of $R^1$ and $R^2$ which are independent of each other is a hydrogen atom, an alkyl group or a cycloalkyl group, each of $R^3$ and $R^4$ which are independent of each other, is a hydrogen atom or an alkyl group, provided that $R^1$ and $R^2$, or $R^2$ and $R^3$ may be bonded to each other to form a cycloalkyl group together with the carbon atoms to which they are bonded, and $X^2$ is a halogen or an anionic residue derived from an acid, which method comprises reacting a 3-halogeno-4,5-dihydroisoxazole compound of formula (1):

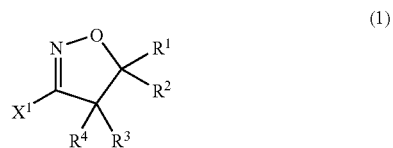

(1)

wherein $R^1$, $R^2$, $R^3$ and $R^4$ are as defined above, and $X^1$ is halogen with thiourea in the presence of an acid.

2. The method for producing a (4,5-dihydroisoxazol-3-yl)thiocarboxamidine salt compound according to claim 1, wherein the acid is inorganic acid.

3. The method for producing a (4,5-dihydroisoxazol-3-yl)thiocarboxamidine salt compound according to claim 1, wherein the acid is hydrochloric acid hydrobromic acid or a mixture thereof.

4. The method for producing a (4,5-dihydroisoxazol-3-yl)thiocarboxamidine salt compound according to claim 1, wherein in formula (1), each of $R^1$ and $R^2$ is an alkyl group, each of and $R^3$ and $R^4$ is a hydrogen atom, and $X^1$ is a chlorine atom.

5. The method for producing a (4,5-dihydroisoxazol-3-yl)thiocarboxamide salt compound according to claim 1, wherein in formula (1), each of $R^1$ and $R^2$ is a methyl group, each of $R^3$ and $R^4$ is a hydrogen atom, and $X^1$ is a chlorine atom.

6. The method for producing a (4,5-dihydroisoxazol-3-yl)thiocarboxamidine salt compound according to claim 1, wherein in formula (1), each of $R^1$ and $R^2$ is an alkyl group each of $R^3$ and $R^4$ is a hydrogen atom, and $X^1$ is a bromine atom.

7. The method for producing a (4,5-dihydroisoxazol-3-yl)thiocarboxamidine salt compound according to claim 1, wherein in formula (1), each of $R^1$ and $R^2$ is a methyl group, each of $R^3$ and $R^4$ is a hydrogen atom, and $X^1$ is a bromine atom.

8. A (4,5-dihydroisoxazol-3-yl)thiocarboxamidine salt compound of formula (2):

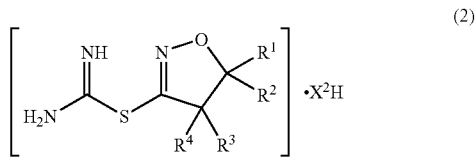

(2)

wherein each of $R^1$ and $R^2$, which are independent of each other, is a hydrogen atom, an alkyl group or a cycloalkyl group, each of $R^3$ and $R^4$ which are independent of each other is a hydrogen atom or an alkyl group provided that $R^1$ and $R^2$, or $R^2$ and $R^3$, may be bonded to each other to form a cycloalkyl group together with the carbon atoms to which they are bonded, and $X^2$ is a halogen or an anionic residue derived from an acid.

9. A (4,5-dihydroisoxazol-3-yl)thiocarboxamidine salt or compound of formula (3):

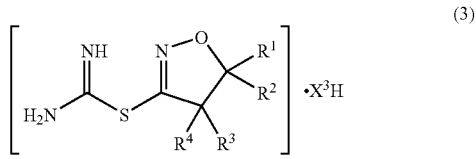

(3)

wherein each of $R^1$ and $R^2$, which are independent of each other is hydrogen atom, an alkyl group or a cycloalkyl group each of $R^3$ and $R^4$, which are independent of each other is a hydrogen atom or an alkyl group, provided that $R^1$ and $R^2$, or $R^2$ and $R^3$, may be bonded to each other to form a cycloalkyl group together with the carbon atoms to which they are bonded, and $X^3$ is a halogen.

10. The (4,5-dihydroisoxazol-3-yl)thiocarboxamidine salt compound according to claim 8, wherein each of $R^1$ and $R^2$ is a methyl group, and each of $R^3$ and $R^4$ is a hydrogen atom.

11. The (4,5-dihydroisoxazol-3-yl)thiocarboxamidine salt compound according to claim 9, wherein each of $R^1$ and $R^2$ is a methyl group, and each of $R^3$ and $R^4$ is a hydrogen atom.

12. [5,5-dimethyl-(4,5-dihydroisoxazol-3-yl)]thiocarboxamidine hydrochloride.

13. [5,5-dimethyl-(4,5-dihydroisoxazol-3-yl)]thiocarboxamidine hydrochloride.

* * * * *